United States Patent
Akagane et al.

(10) Patent No.: US 10,624,692 B2
(45) Date of Patent: Apr. 21, 2020

(54) POWER SUPPLY APPARATUS, OPERATING SYSTEM INCLUDING THE POWER SUPPLY APPARATUS, AND METHOD OF OPERATING THE POWER SUPPLY APPARATUS

(71) Applicant: OLYMPUS CORPORATION, Hachioji-shi, Tokyo (JP)

(72) Inventors: Tsunetaka Akagane, Hachioji (JP); Ko Kawashima, Musashino (JP); Tsuyoshi Hayashida, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/609,194

(22) Filed: May 31, 2017

(65) Prior Publication Data

US 2017/0258515 A1    Sep. 14, 2017

Related U.S. Application Data

(63) Continuation of application No. PCT/JP2016/063669, filed on May 6, 2016.

(30) Foreign Application Priority Data

Sep. 25, 2015   (JP) .................................. 2015-188490

(51) Int. Cl.
    *A61B 18/12*    (2006.01)
    *A61B 17/32*    (2006.01)
    (Continued)

(52) U.S. Cl.
    CPC .. *A61B 18/1206* (2013.01); *A61B 17/320092* (2013.01); *A61B 18/1445* (2013.01);
    (Continued)

(58) Field of Classification Search
    CPC ........ A61B 18/1442; A61B 2018/0019; A61B 2018/00875; A61B 2018/00994; A61B 2018/126
    See application file for complete search history.

(56) References Cited

U.S. PATENT DOCUMENTS

| 5,318,563 | A  | * | 6/1994 | Malis | ...................... A61B 18/12 |
|           |    |   |        |       | 606/34 |
| 7,041,096 | B2 | * | 5/2006 | Malis | .................. A61B 18/1206 |
|           |    |   |        |       | 606/34 |

(Continued)

FOREIGN PATENT DOCUMENTS

| CN | 103987333 A | 8/2014 |
| JP | H08-299351 A | 11/1996 |

(Continued)

OTHER PUBLICATIONS

Aug. 2, 2016 International Search Report issued in Patent Application No. PCT/JP2016/063669.

(Continued)

*Primary Examiner* — Ronald Hupczey, Jr.
(74) *Attorney, Agent, or Firm* — Oliff PLC

(57) ABSTRACT

A power supply apparatus is for a treatment instrument including a probe having electrical conductivity which vibrates, a grasping member that is opened and closed with respect to the probe and an electrode provided in the grasping member. The power supply apparatus supplies high-frequency power between the probe and the electrode. The power supply apparatus includes a resistance acquisition circuit which repeatedly acquires a resistance value of electrical resistance between the probe and the electrode, a condition determination circuit which acquires the number of times the resistance value satisfies a predetermined condition while the probe is vibrating and power is supplied between the probe and the electrode, and a determination (Continued)

circuit which determines whether or not the probe and the electrode are electrically short-circuited based on the number of times.

13 Claims, 12 Drawing Sheets

(51) Int. Cl.
*A61B 18/14* (2006.01)
*A61B 18/00* (2006.01)
*A61B 17/00* (2006.01)

(52) U.S. Cl.
CPC ............. *A61B 2017/0003* (2013.01); *A61B 2017/00123* (2013.01); *A61B 2017/320094* (2017.08); *A61B 2017/320095* (2017.08); *A61B 2018/0063* (2013.01); *A61B 2018/00601* (2013.01); *A61B 2018/00607* (2013.01); *A61B 2018/00666* (2013.01); *A61B 2018/00875* (2013.01); *A61B 2018/00898* (2013.01); *A61B 2018/00922* (2013.01); *A61B 2018/00952* (2013.01); *A61B 2018/00994* (2013.01); *A61B 2018/126* (2013.01); *A61B 2018/1293* (2013.01)

(56) References Cited

U.S. PATENT DOCUMENTS

| | | | | |
|---|---|---|---|---|
| 7,651,492 | B2* | 1/2010 | Wham | A61B 18/1206 606/34 |
| 7,678,105 | B2* | 3/2010 | McGreevy | A61B 18/1442 606/32 |
| 7,717,914 | B2* | 5/2010 | Kimura | A61B 18/1442 606/51 |
| 8,663,223 | B2* | 3/2014 | Masuda | A61B 17/320092 606/169 |
| 2005/0070800 | A1* | 3/2005 | Takahashi | A61B 17/320092 600/459 |
| 2009/0254080 | A1 | 10/2009 | Honda | |
| 2012/0101493 | A1* | 4/2012 | Masuda | A61B 17/320092 606/34 |
| 2014/0236140 | A1* | 8/2014 | Honda | A61B 18/04 606/34 |
| 2015/0265347 | A1 | 9/2015 | Yates et al. | |

FOREIGN PATENT DOCUMENTS

| | | |
|---|---|---|
| JP | 2004-195192 A | 7/2004 |
| JP | 2009-247887 A | 10/2009 |
| WO | 2011/089769 A1 | 7/2011 |

OTHER PUBLICATIONS

Aug. 2, 2016 Written Opinion issued in Patent Application No. PCT/JP2016/063669.

Jun. 13, 2018 Extended European Search Report issued in European Patent Application No. 16848353.5.

Mar. 4, 2019 Office Action issued in Chinese Patent Application No. 201680003484.2.

Nov. 5, 2019 Office Action issued in Chinese Application No. 201680003484.2.

* cited by examiner

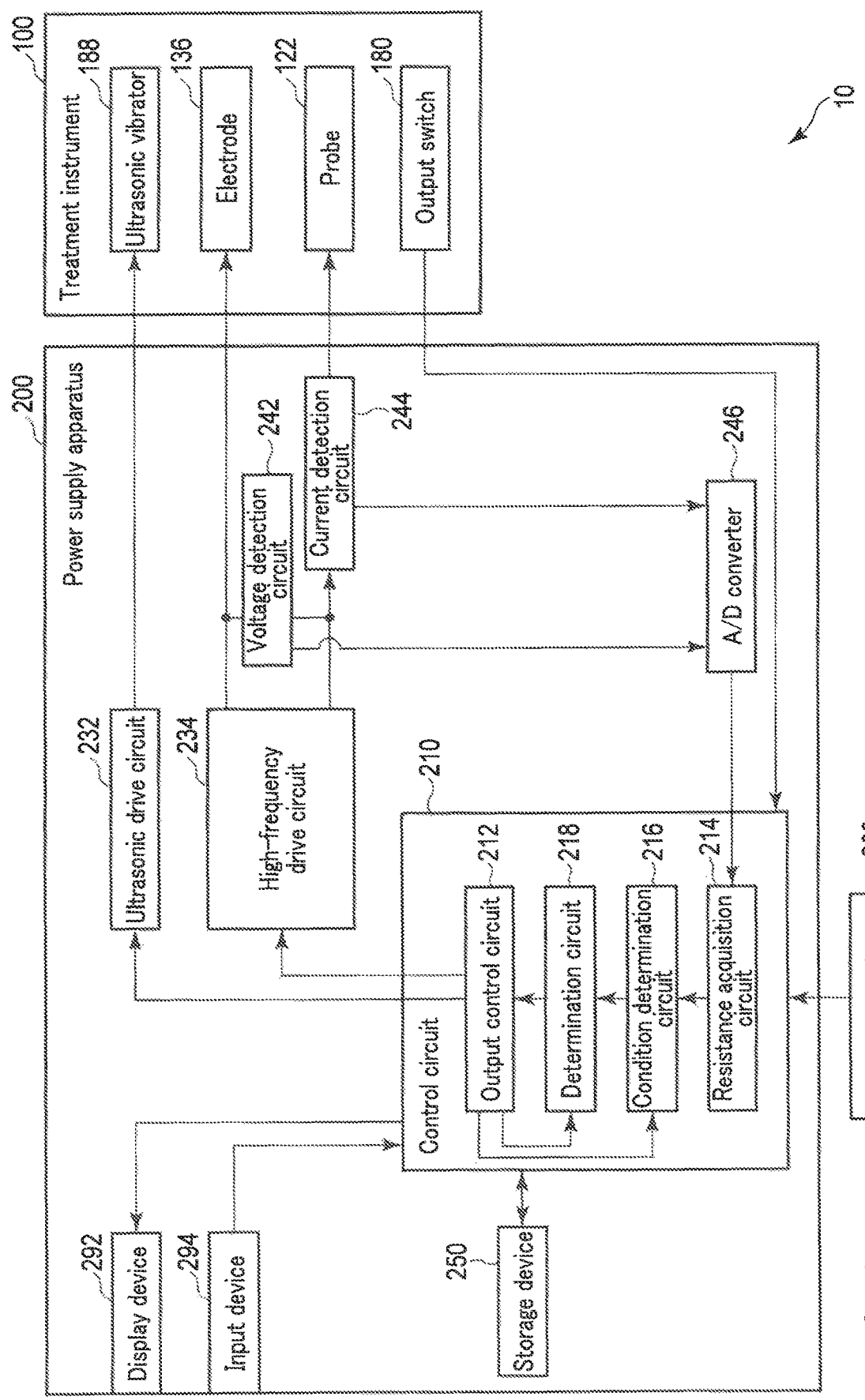
F I G. 4

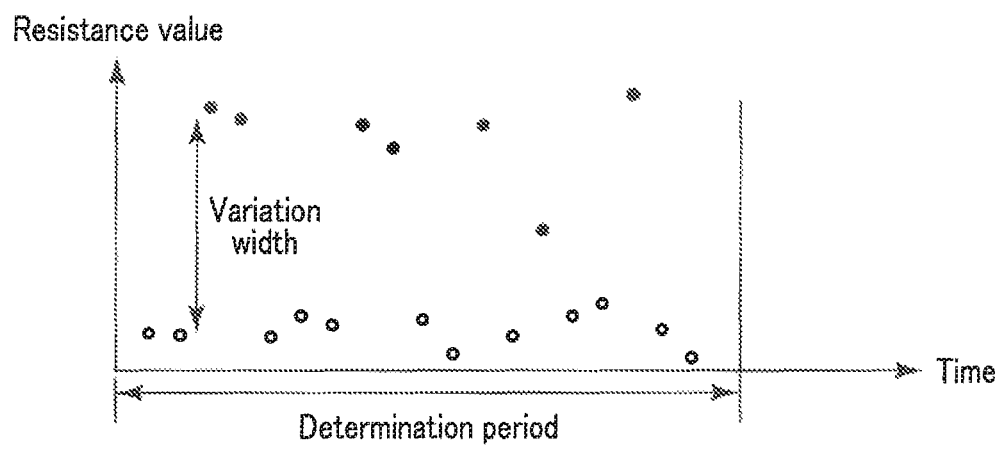
F I G. 9

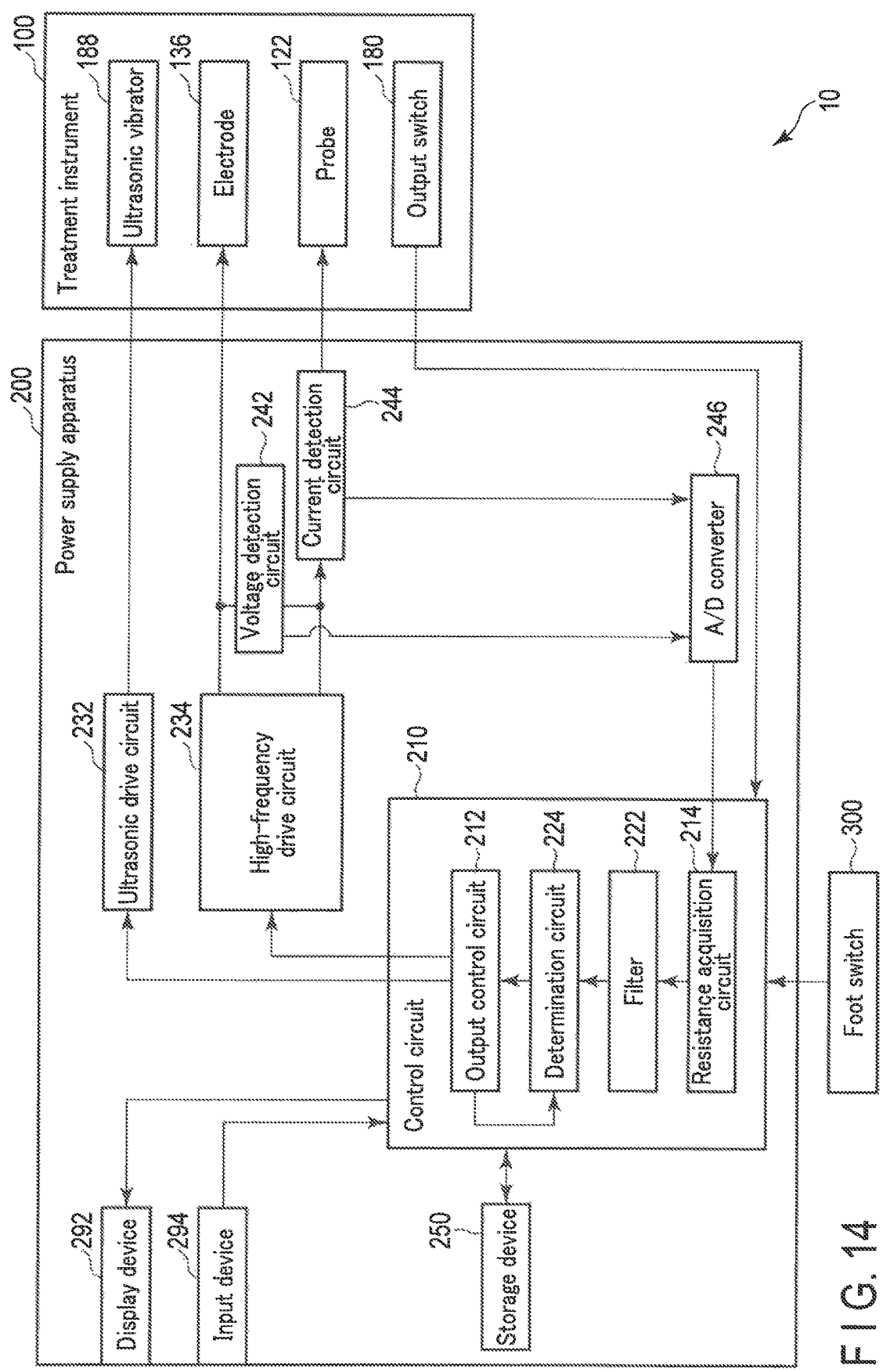
F I G. 14

POWER SUPPLY APPARATUS, OPERATING SYSTEM INCLUDING THE POWER SUPPLY APPARATUS, AND METHOD OF OPERATING THE POWER SUPPLY APPARATUS

CROSS-REFERENCE TO RELATED APPLICATIONS

This application is a Continuation Application of PCT Application No. PCT/JP2016/063669, filed May 6, 2016 and based upon and claiming the benefit of priority from prior Japanese Patent Application No. 2015-188490, filed Sep. 25, 2015, the entire contents of all of which are incorporated herein by reference.

BACKGROUND OF THE INVENTION

1. Field of the Invention

The present invention relates to a power supply apparatus, an operating system including the power supply apparatus, and a method of operating the power supply apparatus.

2. Description of the Related Art

Treatment instruments for treating biological tissue using ultrasonic vibration and high-frequency power are known. For example, Jpn. Pat. Appln. KOKAI Publication No. 2009-247887 discloses a technology on such a treatment instrument. The treatment instrument disclosed in Jpn. Pat. Appln. KOKAI Publication No. 2009-247887 includes an ultrasonically vibrating probe and a jaw for grasping biological tissue to be treated together with the probe. The probe and jaw each function as an electrode to supply power to the biological tissue. Jpn. Pat. Appln. KOKAI Publication No. 2009-247887 discloses that when the probe and jaw are brought into contact and electrically short-circuited, the short circuit is detected to stop outputting ultrasonic vibration and high-frequency power.

Furthermore, Jpn. Pat. Appln. KOKAI Publication No. 2004-195192 discloses a technology on a treatment instrument for treating biological tissue using high-frequency power. Jpn. Pat. Appln. KOKAI Publication No. 2004-195192 also discloses a short-circuit detection method executed when a probe and a jaw are separated and short-circuited repeatedly. In this method, the measured impedance values between the probe and jaw are compared with a plurality of threshold values to determine whether or not a short circuit occurs.

BRIEF SUMMARY OF THE INVENTION

According to an aspect of the present invention, a power supply apparatus for a treatment instrument that includes a probe having electrical conductivity which vibrates, a grasping member that is opened and closed with respect to the probe and an electrode provided in the grasping member, supplies high-frequency power between the probe and the electrode, the apparatus including a resistance acquisition circuit which repeatedly acquires a resistance value of electrical resistance between the probe and the electrode; a condition determination circuit which acquires the number of times the resistance value satisfies a predetermined condition while the probe is vibrating and power is supplied between the probe and the electrode; and a determination circuit which determines whether or not the probe and the electrode are electrically short-circuited based on the acquired number of times.

According to an aspect of the present invention, a power supply apparatus for a treatment instrument that includes a probe having electrical conductivity which vibrates, a grasping member that is opened and closed with respect to the probe and an electrode provided in the grasping member, supplies high-frequency power between the probe and the electrode, the apparatus including a resistance acquisition circuit which repeatedly acquires a resistance value of electrical resistance between the probe and the electrode; and a determination circuit which determines that the probe and the electrode are electrically short-circuited when a signal of the resistance value, which is filtered by a filter and whose cut-off frequency is determined based on a vibration frequency of the probe, satisfies a predetermined condition for a predetermined period, while the probe is vibrating and power is supplied between the probe and the electrode.

According to an aspect of the present invention, an operating system includes the above-mentioned power supply apparatus; and the treatment instrument.

According to an aspect of the present invention, a method of operating a power supply apparatus for a treatment instrument that includes a probe having electrical conductivity which vibrates, a grasping member that is opened and closed with respect to the probe and an electrode provided in the grasping member, the apparatus supplying high-frequency power between the probe and the electrode, causes the power supply apparatus to: repeatedly acquire a resistance value of electrical resistance between the probe and the electrode; acquire the number of times the resistance value satisfies a predetermined condition while the probe is vibrating and power is supplied between the probe and the electrode; and determine whether the probe and the electrode are electrically short-circuited based on the acquired number of times.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 4 is a schematic block diagram showing an example of a configuration of an operating system according to a first embodiment.

FIG. 9 is a schematic diagram for explaining a short-circuit determination process according to a third embodiment.

FIG. 14 is a schematic block diagram showing an example of a configuration of an operating system according to the fourth embodiment.

DETAILED DESCRIPTION OF THE INVENTION

First Embodiment

A first embodiment of the present invention will be described with reference to the drawings.

<Configuration of Operating System>

Figure 1:
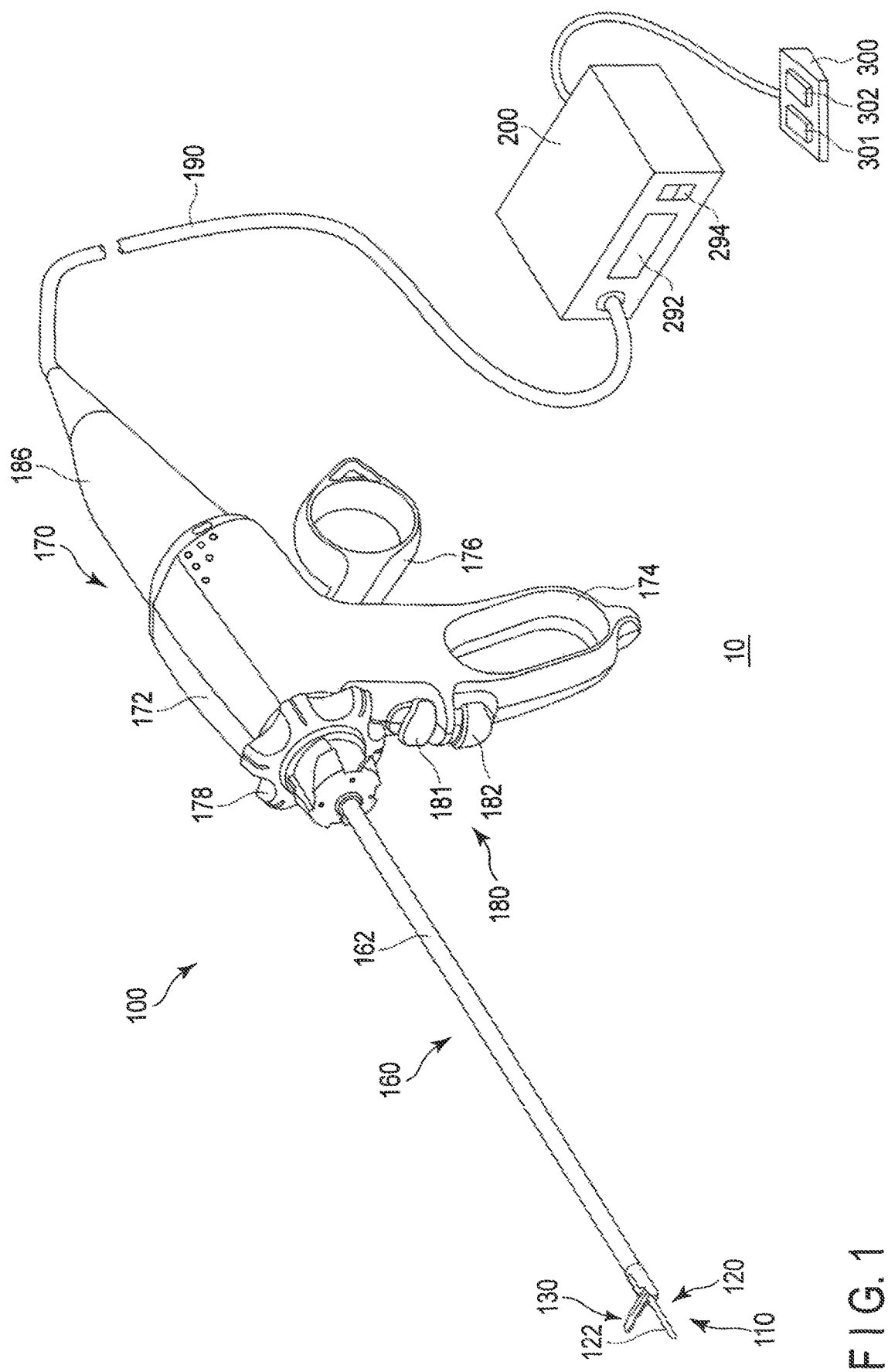
FIG. 1 is a schematic view showing an example of a configuration of an operating system according to one embodiment.

FIG. 1 is a schematic view showing an example of a configuration of an operating system 10 according to the first embodiment. As shown in this figure, the operating system 10 includes a treatment instrument 100, a power supply apparatus 200, and a foot switch 300.

The treatment instrument 100 includes a treatment section 110, a shaft 160, and an operation section 170. Hereinafter, the treatment section 110 side will be referred to as a distal side and the operation section 170 side will be referred to as a proximal side. The treatment instrument 100 is configured to grasp an object to be treated by the treatment section 110. The object to be treated is biological tissue, such as membranous tissue, internal organs, bone, and blood vessels.

In the operating system 10, a high-frequency voltage is applied to the grasped biological tissue to seal and coagulate the biological tissue. Furthermore, the operating system 10 cuts the biological tissue grasped by the treatment section 110 using ultrasonic vibration while applying a high-frequency voltage thereto, sealing the biological tissue, or the like.

The shaft 160 includes a hollow sheath 162. In the sheath 162, a vibration transmission member 120 that vibrates in its longitudinal direction is disposed to transmit ultrasonic vibration. The proximal end of the vibration transmission member 120 is located in the operation section 170. The distal side of the vibration transmission member 120 protrudes from the sheath 162 and is located in the treatment section 110. The distal side of the vibration transmission member 120 includes a probe 122. The vibration transmission member 120 has electrical conductivity.

The treatment section 110 includes a jaw 130. The jaw 130 opens and closes with respect to the probe 122 that is a distal end portion of the vibration transmission member 120. With this open and close operation, the probe 122 and jaw 130 grasp biological tissue to be treated. Part of the jaw 130 has electrical conductivity. Thus, part of the probe 122 and part of the jaw 130 serve as a bipolar electrode to apply a high-frequency voltage to the grasped biological tissue.

The operation section 170 includes an operation section main body 172, a fixed handle 174, a movable handle 176, a rotation knob 178, and an output switch 180. The operation section main body 172 includes an ultrasonic vibrator unit 186. The ultrasonic vibrator unit 186 includes an ultrasonic vibrator. The proximal side of the vibration transmission member 120 is connected to the ultrasonic vibrator. The ultrasonic vibration generated from the ultrasonic vibrator is transmitted by the vibration transmission member 120. In the first embodiment, the ultrasonic vibrator generates ultrasonic waves having a frequency of about 47 kHz, for example. The frequency is not limited to 47 kHz, but the ultrasonic vibrator may generate ultrasonic waves having whatever frequency if it is suitable for treatment.

The fixed handle 174 is fixed to the operation section main body 172. The movable handle 176 is displaced from the operation section main body 172. The movable handle 176 is connected to a wire or a rod inserted through the shaft 160. The wire or rod is connected to the jaw 130. The operation of the movable handle 176 is transmitted to the jaw 130 via the wire or rod. The jaw 130 is displaced from the probe 122 in response to the operation of the movable handle 176. The rotation knob 178 is a knob to rotate a section on the distal side of the rotation knob 178. The treatment section 110 and shaft 160 rotate with the rotation of the rotation knob 178, and the angle of the treatment section 110 is adjusted.

The output switch 180 includes a first output button 181 and a second output button 182. The first output button 181 is a button that is depressed when the treatment section 110 applies high-frequency power and ultrasonic vibration to biological tissue to be treated. The power supply apparatus 200 detects the depression of the button to apply a high-frequency voltage between the probe 122 and jaw 130 and to drive the ultrasonic vibrator. Consequently, the biological tissue grasped by the treatment section 110 is coagulated or sealed and cut. The second output button 182 is a button that is depressed when the treatment section 110 applies only high-frequency power to biological tissue to be treated. The power supply apparatus 200 detects the depression of the button to apply a high-frequency voltage between the probe 122 and jaw 130 and to inhibit the ultrasonic vibrator from being driven. Consequently, the biological tissue grasped by the treatment section 110 is coagulated or sealed without being cut.

One end of a cable 190 is connected to the proximal side of the operation section 170. The other end of the cable 190 is connected to the power supply apparatus 200. The power supply apparatus 200 includes a display device 292 to display various states of the operating system 10. The display device 292 includes a liquid crystal display, a monitor lamp including an LED, or the like. The power supply apparatus 200 also includes an input device 294 to input, e.g. setting information on the operating system 10.

The input device 294 includes a button switch, a dial, a keyboard, a touch panel, or the like.

The foot switch 300 is connected to the power supply apparatus 200. The foot switch 300 includes a first pedal 301 and a second pedal 302. The first pedal 301 has the same function as that of the first output button 181 included in the operation section 170. The second pedal 302 has the same function as that of the second output button 182 included in the operation section 170. The operating system 10 may include one or both of the output switch 180 and the foot switch 300.

Figure 2:
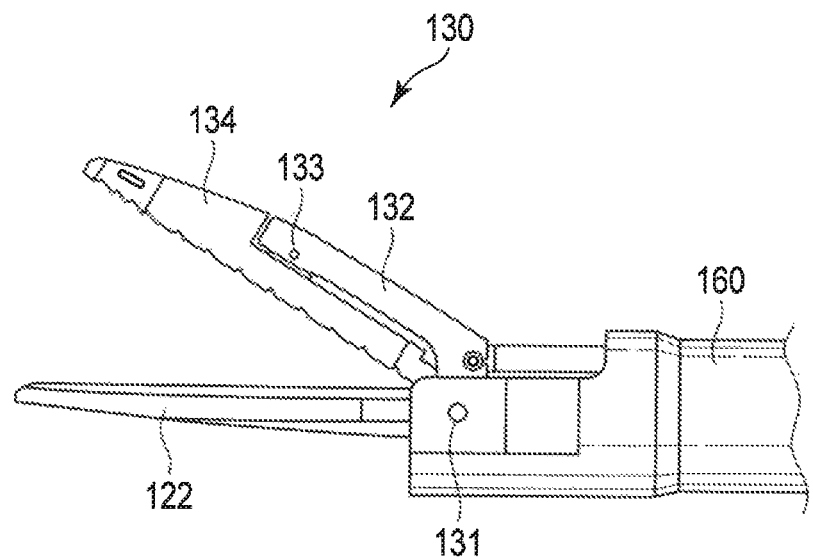
FIG. 2 is a schematic side view showing an example of a treatment section of the operating system according to the one embodiment.

An example of a configuration of the treatment section 110 will be described further with reference to FIGS. 2 and 3. FIG. 2 is a side view of the treatment section 110. The probe 122 that is a distal end portion of the vibration transmission member 120 protrudes from the distal end of the shaft 160. The jaw 130 includes a supporting member 132 that is rotatably provided at the distal end portion of the shaft 160 on a first rotation axis 131 as a central axis. A second rotation axis 133 is provided close to the distal end of the supporting member 132, and a grasping member 134 is rotatably provided on the second rotation axis as a central axis. The grasping member 134 can rotate with respect to the supporting member 132 in accordance with the position of the supporting member 132. Therefore, the treatment section 110 allows biological tissue to be grasped at the same pressure on both of the distal side and the proximal side, even though the biological tissue varies in thickness between the distal side and the proximal side. Applying a uniform pressure to biological tissue to be treated brings about an advantage of sealing, coagulating, and cutting the biological tissue with stability.

Figure 3:
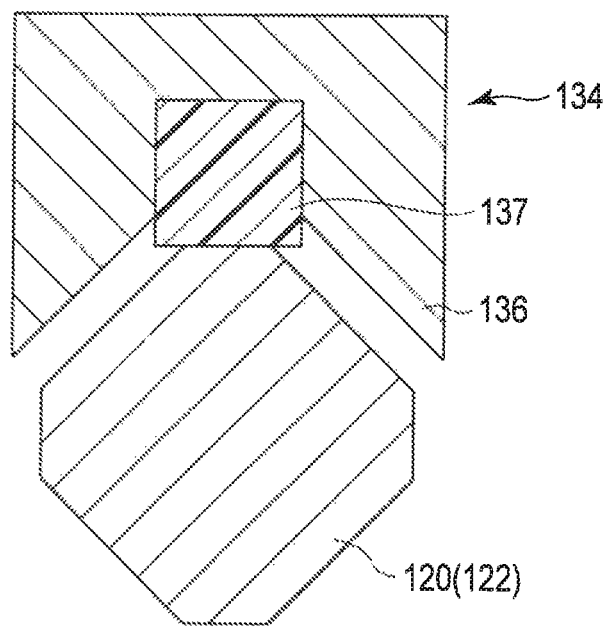
FIG. 3 is a schematic sectional view taken perpendicularly to the longitudinal direction of the treatment section of the operating system according to the one embodiment.

FIG. 3 is a sectional view of the treatment section 110, taken perpendicularly to the longitudinal axis of the vibration transmission member 120. In this figure, the vibration transmission member 120 and the grasping member 134 of the jaw 130 are closed. As shown in FIG. 3, the section of the vibration transmission member 120 in the treatment section 110, or the section of the probe 122, is octagonal. The grasping member 134 includes an electrode 136 and a pad member 137. The pad member 137 is formed of insulating material such as fluororesin. When the treatment section 110 is closed, the probe 122 and the pad member 137 are brought into contact to form a gap between the probe 122 and the electrode 136. Thus, no short circuit is caused between the probe 122 and the electrode 136. The outside portion of the grasping member 134, or the portion that is not opposed to the probe 122, is electrically insulated.

When the treatment section 110 grasps biological tissue and applies a high-frequency voltage to it during the use of the operating system 10, current flows through the biological tissue in the gap portion. Accordingly, the biological tissue through which current has flowed generates heat. This heat allows the biological tissue to be coagulated or sealed. When the ultrasonic vibrator vibrates, the probe 122 vibrates in its longitudinal direction, and friction with the probe 122 causes the biological tissue to be cut in a portion between the pad member 137 and the probe 122.

FIG. 4 is a schematic block diagram showing an example of the configuration of the operating system 10 with an emphasis on the power supply apparatus 200. The power supply apparatus 200 includes a control circuit 210 to control the operation of each section of the power supply apparatus 200. The power supply apparatus 200 also includes an ultrasonic drive circuit 232, a high-frequency drive circuit 234, a voltage detection circuit 242, a current detection circuit 244, an A/D converter 246, a storage device 250, a display device 292, and an input device 294.

The ultrasonic drive circuit 232 is connected to the ultrasonic vibrator 188 included in the ultrasonic vibrator unit 186 of the treatment instrument 100. The ultrasonic drive circuit 232 supplies power to the ultrasonic vibrator 188 to cause the ultrasonic vibrator 188 to generate ultrasonic vibration under the control of the control circuit 210. The ultrasonic vibration generated from the ultrasonic vibrator 188 is transmitted to the distal end of the vibration transmission member 120, or to the probe 122 through the vibration transmission member 120.

The high-frequency drive circuit 234 outputs high-frequency power to be supplied to the treatment instrument 100 under the control of the control circuit 210. In other words, the high-frequency drive circuit 234 is connected to the electrode 136 included in the grasping member 134 of the jaw 130 and probe 122 to supply high-frequency power between the electrode 136 and probe 122.

The current detection circuit 244 is inserted between the high-frequency drive circuit 234 and the treatment instrument 100 to output an analog signal indicating a current value to be output from the high-frequency drive circuit 234. The voltage detection circuit 242 outputs an analog signal indicating an output voltage of the high-frequency drive circuit 234.

The output signals of the current detection circuit 244 and the voltage detection circuit 242 are input to the A/D converter 246. The A/D converter 246 converts the input analog signals into digital signals and transmits them to the control circuit 210. Thus, the control circuit 210 acquires information of the output voltage and output current of the high-frequency drive circuit 234.

The storage device 250 includes a semiconductor memory, a hard disk, or the like. The storage device 250 stores programs used in the control circuit 210, various parameters used for computation in the control circuit 210, tables, and the like.

The control circuit 210 includes an output control circuit 212, a resistance acquisition circuit 214, a condition determination circuit 216, and a determination circuit 218.

The output control circuit 212 is connected to the ultrasonic drive circuit 232 and high-frequency drive circuit 234. The output control circuit 212 controls the outputs of the ultrasonic drive circuit 232 and high-frequency drive circuit 234. For example, the output control circuit 212 switches on and off the outputs of the ultrasonic drive circuit 232 and high-frequency drive circuit 234 to set output intensity and the like. During the treatment, the ultrasonic drive circuit 232 and high-frequency drive circuit 234 are activated, and the temperature of the vibration transmission member 120 rises. Accordingly, the vibration system including the ultrasonic vibrator 188 and vibration transmission member 120 varies in its resonant frequency. The output control circuit 212 may vary the output frequency of the ultrasonic drive circuit 232 according to the variation in the resonant frequency. The output control circuit 212 also transmits information on the control of outputs of the ultrasonic drive circuit 232 and high-frequency drive circuit 234 to the condition determination circuit 216 and determination circuit 218.

The resistance acquisition circuit 214 acquires information on the voltage and current values of outputs of the high-frequency drive circuit 234 from the A/D converter 246. Based on the acquired voltage and current values, the resistance acquisition circuit 214 computes a resistance value of electrical resistance between the probe 122 and the electrode 136. The resistance acquisition circuit 214 transmits the computed resistance value to the condition determination circuit 216.

The condition determination circuit 216 determines whether or not the resistance value acquired from the resistance acquisition circuit 214 satisfies a given condition, and counts the number of times the resistance value satisfies the given condition. It is particularly during the activation of the ultrasonic drive circuit 232, or during the vibration of the probe 122 that the number of times the resistance value satisfies a given condition is counted. It is also during the activation of the high-frequency drive circuit 234, or during the supply of power between the probe 122 and the electrode 136 that the number of times the resistance value satisfies a given condition is counted. The condition determination circuit 216 can determine, based on the output information acquired from the output control circuit 212, whether or not the probe 122 is vibrating and whether or not power is supplied between the probe 122 and the electrode 136. The condition determination circuit 216 transmits the number of times the resistance value satisfies the given condition to the determination circuit 218.

The determination circuit 218 determines whether or not the probe 122 and the electrode 136 are electrically short-circuited to each other based on the number of times the resistance value satisfies the given condition, which is acquired from the condition determination circuit 216. To determine it, the determination circuit 218 may use the output information acquired from the output control circuit 212. When the determination circuit 218 determines that the probe 122 and the electrode 136 are electrically short-circuited to each other, it transmits information to that effect to the output control circuit 212. The output control circuit 212, which has received the information to the effect that the probe 122 and the electrode 136 are electrically short-circuited to each other, inhibits, for example, the ultrasonic drive circuit 232 and high-frequency drive circuit 234 from outputting a signal. Furthermore, when it is determined that the probe 122 and the electrode 136 are electrically short-circuited to each other, the control circuit 210 may display the information to that effect on the display device 292.

The output control circuit 212, resistance acquisition circuit 214, condition determination circuit 216, determination circuit 218, etc. include, for example, integrated circuits, such as a central processing unit (CPU), an application specific integrated circuit (ASIC), and a field programmable gate array (FPGA). The output control circuit 212, resistance acquisition circuit 214, condition determination circuit 216, determination circuit 218, etc. can be each configured by, for example, a single integrated circuit or by a plurality of integrated circuits in combination. Two or more of the output control circuit 212, resistance acquisition circuit 214, condition determination circuit 216, and determination circuit 218 can be configured by, for example, a single integrated circuit. The control circuit 210 as a whole can be configured by a single integrated circuit, etc. The control circuit 210 operates in accordance with the programs recorded in, for example, the storage device 250 and a recording area of the control circuit 210.

<Overview of Operation of Operating System>

An operation of the operating system 10 will be described. An operator operates the input device 294 of the power supply apparatus 200 to set the output conditions of the treatment instrument, such as output power of high-frequency energy and output power of ultrasonic energy.

The treatment section 110 and the shaft 160 are inserted into an abdominal cavity through an abdominal wall using, for example, a trocar. The operator operates the movable handle 176 to open and close the treatment section 110 and grasps biological tissue to be treated with the probe 122 and the jaw 130. When the operator grasps the biological tissue by the treatment section 110, he or she operates the output switch 180. For example, the control circuit 210 of the power supply apparatus 200 detects that the first output button 181 is depressed and gives a drive-related instruction to the ultrasonic drive circuit 232 and the high-frequency drive circuit 234.

Under the control of the control circuit, the high-frequency drive circuit 234 applies a high-frequency voltage to the probe 122 and the electrode 136 of the jaw 130 of the treatment section 110 to cause a high-frequency current to flow through the biological tissue to be treated. If the high-frequency current flows, the biological tissue becomes an electrical resistor and thus generates heat and its temperature rises. The temperature of this biological tissue is about 100° C., for example. Accordingly, protein is denaturated to coagulate and seal the biological tissue.

The ultrasonic drive circuit 232 drives the ultrasonic vibrator 188 under the control of the control circuit 210. As a result, the probe 122 vibrates with an ultrasonic frequency in its longitudinal direction. The temperature of the biological tissue is risen by friction heat between the biological tissue and the probe 122. Thus, protein is denaturated to coagulate and seal the biological tissue. The effectiveness of sealing the biological tissue by the ultrasonic vibration is less than that of sealing it by applying a high-frequency voltage. The temperature of the biological tissue reaches about 200° C., for example. Accordingly, the biological tissue is broken and cut. Thus, the biological tissue grasped by the treatment section 110 is cut while being coagulated and sealed.

The user who has confirmed that the biological tissue was cut operates the output switch 180 to stop the output. The control circuit 210 that has detected the user's operation stops the outputs of the ultrasonic drive circuit 232 and high-frequency drive circuit 234. The user confirms that the treatment is completed and pulls the treatment section 110 and the shaft 160 out of the abdominal cavity. The treatment of the biological tissue is thus completed.

<Short-Circuit Determination Process>

The power supply apparatus 200 of the first embodiment includes a mechanism of performing error processing when a short circuit occurs between the probe 122 and the electrode 136. The error processing may include, for example, a process of alerting a user or a process of stopping the output.

For example, when the pad member 137 is worn or part of the pad member 137 peels off, a short circuit is likely to occur between the probe 122 and the electrode 136. If a short circuit occurs between the probe 122 and the electrode 136, the probe 122 or the grasping member 134 could be damaged in a short-circuited portion. Due to this damage, there is a risk of that the probe 122 or the grasping member 134 being significantly damaged.

In the first embodiment, it is considered that a short circuit can be detected appropriately even while the probe 122 in particular is ultrasonically vibrating. In other words, while the probe 122 is ultrasonically vibrating, a state in which the probe 122 and the electrode 136 are short-circuited and a state in which they are not short-circuited may be changed during a short period due to the vibration. In this case, too, the first embodiment allows the presence or absence of a short circuit to be determined appropriately.

Figure 5:
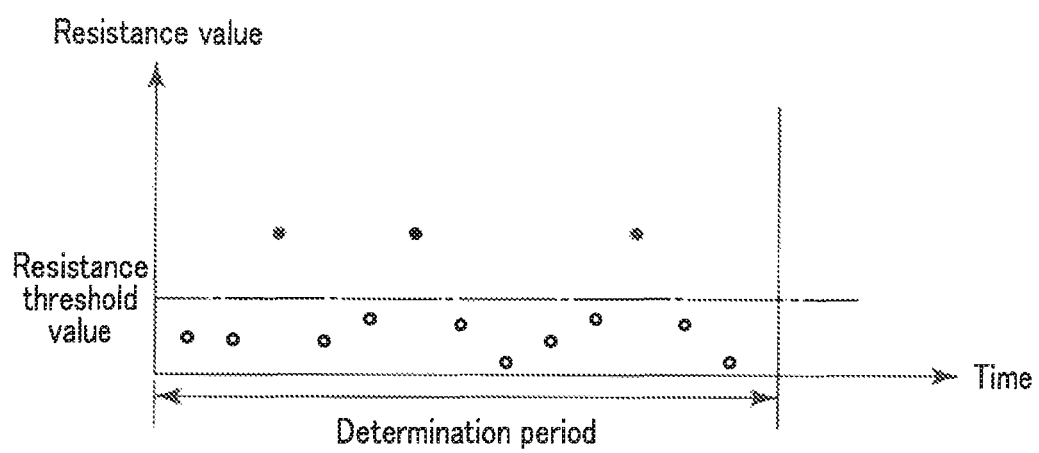
FIG. 5 is a schematic diagram for explaining a short-circuit determination process according to the first embodiment.

FIG. 5 shows time variations of the value (resistance value) of electrical resistance between the probe 122 and the electrode 136 in the state in which the probe 122 and the electrode 136 are short-circuited. As shown in FIG. 5, the resistance value is generally lower than a predetermined threshold value (resistance threshold value) but may become instantaneously larger than the threshold value. These variations are caused by the vibration of the probe 122. In the first embodiment, when the number of times a resistance value, that is lower than the resistance threshold value, is counted during a predetermined determination period and is found to be larger than the number of times of the predetermined reference, it is determined that the probe 122 and the electrode 136 are short-circuited. This determination period is longer than the vibration period of the probe 122. Furthermore, it is desirable that the interval to acquire the resistance value, or the sampling time interval be shorter than the vibration period of the probe 122, but the sampling time interval is not limited to this. Even though the sampling time interval is longer than the vibration period, the operation of the first embodiment can be carried out. However, it is necessary to set the sampling time interval shorter than the determination period.

Figure 6:
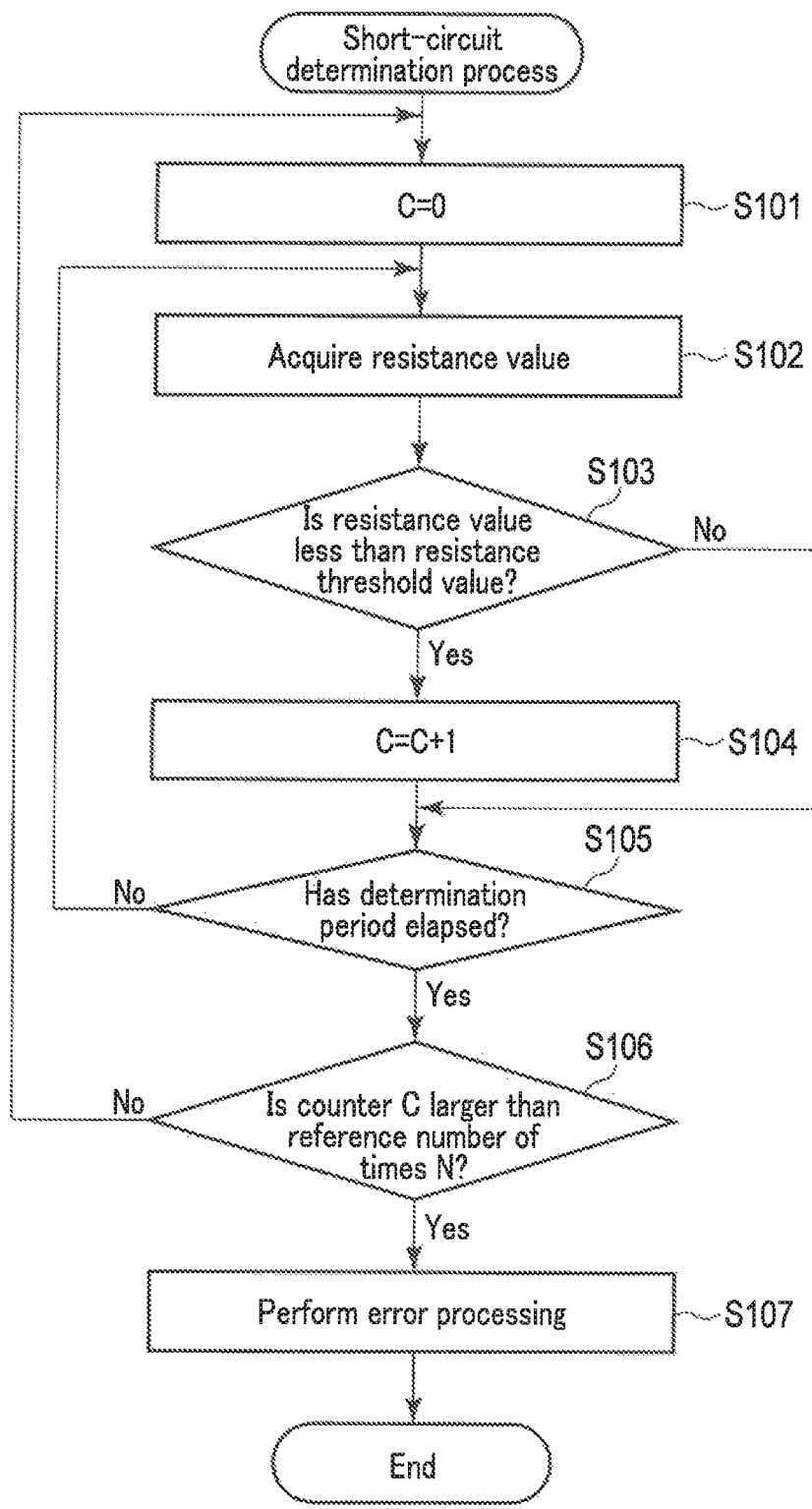
FIG. 6 is a schematic flowchart showing an example of the short-circuit determination process according to the first embodiment.

A short-circuit determination process according to the first embodiment will be described with reference to the flowchart shown in FIG. 6. The short-circuit determination process shown in FIG. 6 is performed while, for example, the first output button 181 is depressed and the ultrasonic drive circuit 232 and the high-frequency drive circuit 234 are operating. In other words, the short-circuit determination process is performed if the probe 122 is vibrating based on the vibration generated by the ultrasonic vibrator 188 and a voltage is applied between the electrode 136 of the grasping member 134 and probe 122. The short-circuit determination process can be performed while, for example, the second output button 182 is depressed and only the high-frequency drive circuit 234 is operating, or even while a voltage is applied between the electrode 136 and the probe 122 but the probe 122 is not vibrating.

In step S101, the control circuit 210 resets a counter C to 0. The counter C is a counter indicating the number of times the resistance value is detected as being less than the resistance threshold value. When the counter C is reset to 0, a timer for measuring a determination period is started.

In step S102, the control circuit 210 acquires a resistance value that is a value of electrical resistance between the probe 122 and the electrode 136. This resistance value is acquired based on detection results of the voltage detection circuit 242 and current detection circuit 244.

In step S103, the control circuit 210 determines whether or not the acquired resistance value is less than a predetermined threshold value (resistance threshold value). When the resistance value is not less than the resistance threshold value, the process proceeds to step S105. When the resistance value is less than the resistance threshold value, the process proceeds to step S104.

In step S104, the control circuit 210 increases the value of the counter C. After that, the process proceeds to step S105.

In step S105, the control circuit 210 acquires a time elapsed from the process of step S101 and determines whether or not a predetermined determination period has elapsed. When the determination period has not elapsed, the process returns to step S102. In other words, the process from step S102 to step S105 is repeated, and the number of times the resistance value is detected as being less than the resistance threshold value is counted as a value of the counter C.

When it is determined in step S105 that the determination period has elapsed, the process proceeds to step S106. In step S106, the control circuit 210 determines whether or not the value of the counter C is larger than the reference number of times N. When the value of the counter C is not larger than the reference number of times N, the process returns to step S101. In other words, the counter C is reset to 0, and the number of cases where the resistance value is less than the resistance threshold value is counted again during the determination period. It is thus determined whether or not the number of times the resistance value is less than the resistance threshold value is found to be larger than the reference number of times N for each determination period.

When the value of the counter C is larger than the reference number of times N in step S106, the process proceeds to step S107. The process proceeds to step S107 when the probe 122 and the electrode 136 are determined as being short-circuited. In step S107, the control circuit 210 performs error processing. As the error processing, for example, the control circuit 210 stops the outputs of the ultrasonic drive circuit 232 and high-frequency drive circuit 234. Instead of stopping the outputs or in conjunction with the stopping, the control circuit 210 may display an alarm indicating an error on the display device 292, sound an alarm, or store an error log in the storage device 250. Thus, the short-circuit determination process is completed.

<Advantages>

According to the first embodiment, a short circuit between the probe 122 and the electrode 136 can be detected appropriately even while the probe 122 is ultrasonically vibrating. As a method of detecting a short circuit, a method of determining that a short circuit occurs when a resistance value to be acquired becomes less than a predetermined resistance threshold value can also be employed. However, when a high-frequency voltage is applied as in the treatment instrument 100 of the first embodiment, generally, there is significant noise, and thus a number of errors are detected. Here, for example, it can be determined that a short circuit occurs when the fact that the resistance value becomes less than a predetermined resistance threshold value continues for a predetermined period. This predetermined period is about several tens of milliseconds through several hundreds of milliseconds, for example. In this determination, however, when a resistance value is measured as shown in FIG. 5, the condition is not satisfied each time the resistance value becomes larger than the resistance threshold value and thus they will not be determined as being short-circuited. In contrast, in the first embodiment, a short-circuit state can be detected even though the resistance value becomes equal to or larger than the resistance threshold value during the determination period. The resistance value becoming equal to or larger than the resistance threshold value in the short-circuit state is caused by the vibration of the probe 122, and is generated periodically in response to the vibration period. For example, while the probe 122 is vibrating with a frequency of 47 kHz, a short circuit is generated in a period of about 0.02 milliseconds. According to the first embodiment, irrespective of such a short period, a short circuit can be detected appropriately.

Second Embodiment

A second embodiment will be described. In the second embodiment, the elements that are different from those of the first embodiment will be described, and the elements that are the same as those of the first embodiment are denoted by the same signs and their descriptions will be omitted. In the first embodiment, it is determined whether or not a short circuit occurs based on the number of times the resistance value becomes less than the resistance threshold value during the determination period. In contrast, the second embodiment will be described below, focusing on the fact that variation of a resistance value is caused by ultrasonic vibration in response to a vibration period.

Figure 7:
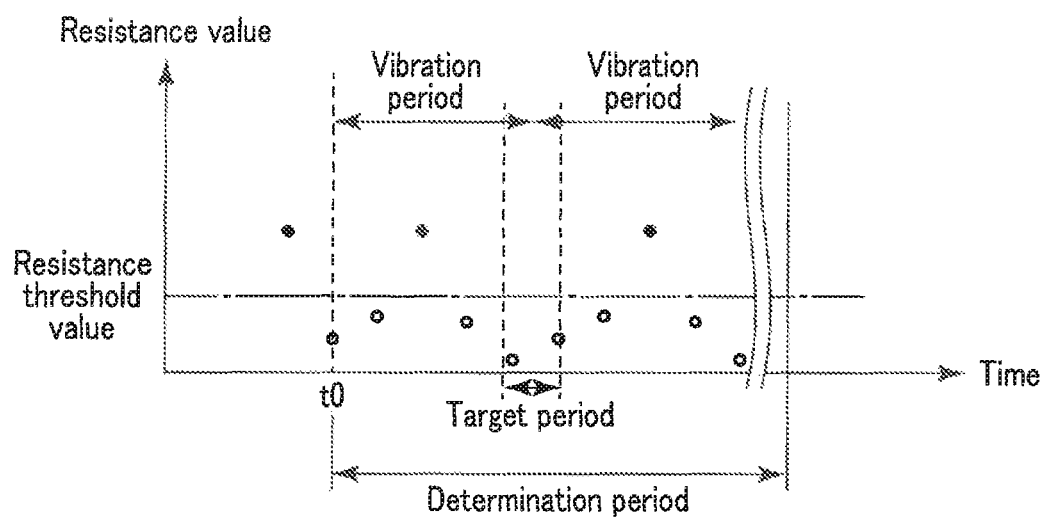
FIG. 7 is a schematic diagram for explaining a short-circuit determination process according to a second embodiment.

As shown in FIG. 7, a target period is set for each vibration period of the probe 122 with reference to time t0 when the resistance value first becomes less than the resistance threshold value. This target period is set in a period including the same phase as time t0. The length of the target period is not limited. The length of the target period can be set to, for example, one fourth of the vibration period.

In the second embodiment, of the resistance values acquired during the target period through the determination period, the resistance values that are less than the resistance threshold value are counted. If the counted number is larger than the reference number of times, it is determined that the probe 122 and the electrode 136 are short-circuited.

Figure 8:
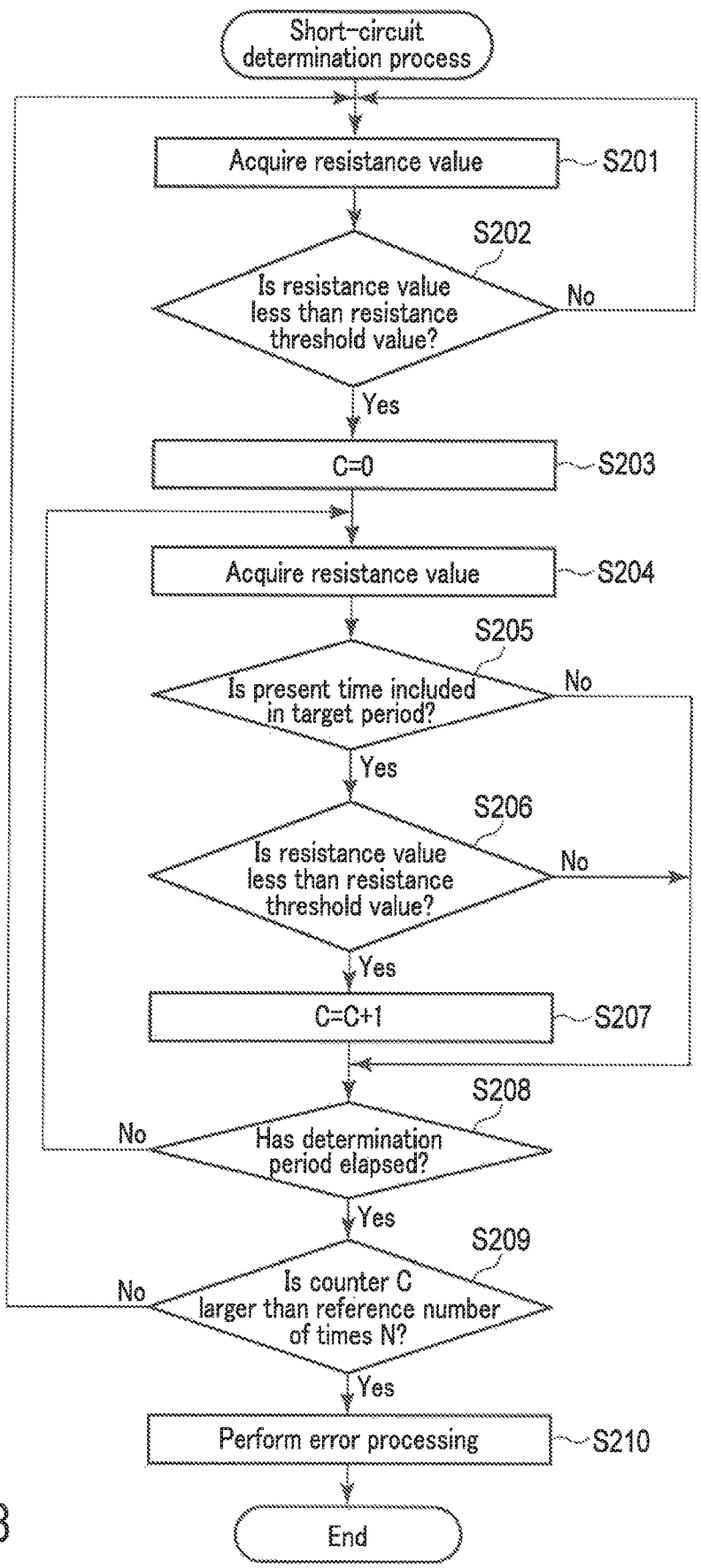
FIG. 8 is a schematic flowchart showing an example of the short-circuit determination process according to the second embodiment.

A short-circuit determination process according to the second embodiment will be described with reference to the flowchart shown in FIG. 8.

In step S201, the control circuit 210 acquires a resistance value that is a value of electrical resistance between the probe 122 and the electrode 136. In step S202, the control circuit 210 determines whether or not the acquired resistance value is less than the resistance threshold value. When the resistance value is not less than the resistance threshold value, the process returns to step S201. When the resistance value is less than the resistance threshold value, the process proceeds to step S203.

In step S203, the control circuit 210 resets the counter C to 0. This corresponds to time t0 shown in FIG. 7 and thus a timer for measuring the determination period is started. Based on this, a target period is determined.

In step S204, the control circuit 210 acquires a resistance value. In step S205, the control circuit 210 determines whether or not the present time is included in the target period for determination. If it is not included in the target period, the process proceeds to step S208. If it is included in the target period, the process proceeds to step S206.

In step S206, the control circuit 210 determines whether or not the acquired resistance value is less than the resistance threshold value. When the resistance value is not less than the resistance threshold value, the process proceeds to step S208. When the resistance value is less than the resistance threshold value, the process proceeds to step S207. In step S207, the control circuit 210 increases the value of the counter C. After that, the process proceeds to step S208.

In step S208, the control circuit 210 determines whether or not a predetermined determination period has elapsed. When the determination period has not elapsed, the process returns to step S204. In other words, the process from step S204 to step S208 is repeated, and the number of times the resistance value is detected as being less than the threshold value is counted as a value of the counter C.

When it is determined in step S208 that the determination period has elapsed, the process proceeds to step S209. In step S209, the control circuit 210 determines whether or not the value of the counter C is larger than the reference number of times N. When the value of the counter C is not larger than the reference number of times N, the process returns to step S201. In other words, when the resistance value is detected again as being less than the resistance threshold value, the counter C is reset to 0, and the number of cases where the resistance value is less than the resistance threshold value is counted again during the target period in the determination period. It is thus determined whether or not the number of times the resistance value is less than the resistance threshold value is larger than the reference number of times N during the target period for each determination period.

When the value of the counter C is larger than the reference number of times N in step S209, the process proceeds to step S210. When the probe 122 and the electrode 136 are determined as being short-circuited, the process proceeds to step S210. In step S210, the control circuit 210 performs error processing.

According to the second embodiment, a short circuit between the probe 122 and the electrode 136 can be detected appropriately even while the probe 122 is ultrasonically vibrating, as in the first embodiment. Since the variation of the resistance value is caused by ultrasonic vibration in response to the vibration period, it is determined whether or not the resistance value is less than the resistance threshold value during a period that includes the same phase as when the resistance value is first detected as being less than the resistance threshold value. This improves the determination more accurately than in the first embodiment.

An example where a target period is set for each vibration period of the probe 122 with reference to time t0 when the resistance value first becomes less than the resistance threshold value, has been so far described, but the present invention is not limited to this example. The target period can be set with reference to the time when the fact that the resistance value becomes less than the resistance threshold value is repeated a predetermined number of times. FIG. 7 shows an example where the target period is set every period of vibration, but the present invention is not limited to this example. One target period can be set every two or more periods. The target period has only to be set in a period during which the probe 122 and the electrode 136 are considered to be in contact with each other periodically in a situation where they are brought into contact with each other or separated from each other by the vibration of the probe 122.

Third Embodiment

A third embodiment will be described. In the third embodiment, the elements that are different from those of the first embodiment will be described, and the elements that are the same as those of the first embodiment are denoted by the same signs and their descriptions will be omitted. In the first embodiment, it is determined whether or not a short circuit occurs based on the number of times the resistance value becomes less than the resistance threshold value during the determination period. In contrast, in the third embodiment, it is determined whether a short circuit occurs based on the number of times the variation width of the resistance value becomes larger than a predetermined variation threshold value.

When the ultrasonically vibrating probe 122 and the electrode 136 are in contact with each other, the resistance value varies widely between the probe 122 and the electrode 136 due to the ultrasonic vibration of the probe 122 as described above. In the third embodiment, therefore, the number of times the variation width of the resistance value becomes larger than a predetermined threshold value as shown in FIG. 9 during a predetermined determination period is counted. When the number of times is larger than the reference number of times, the probe 122 and the electrode 136 are determined as being short-circuited.

Figure 10:
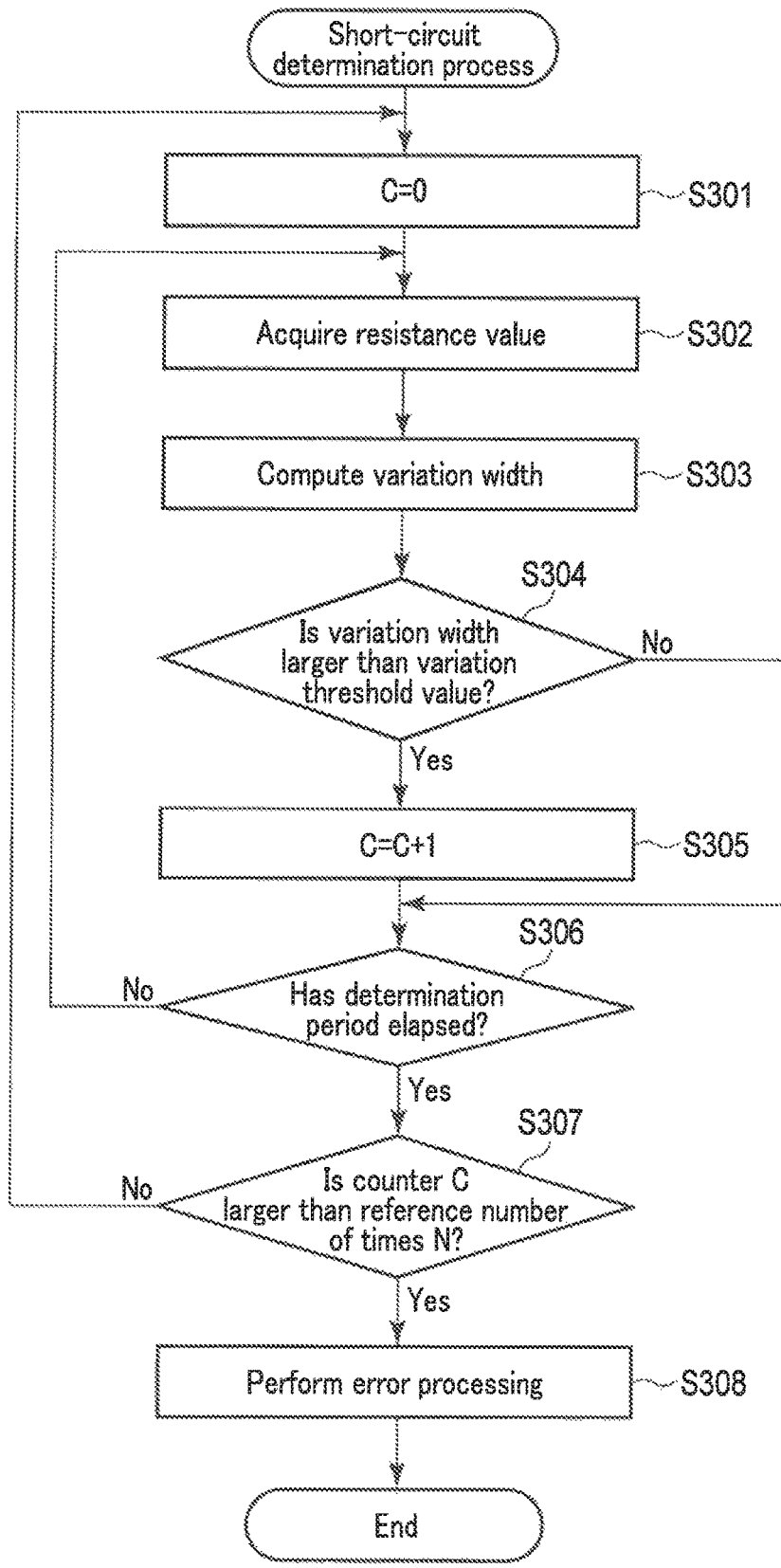
FIG. 10 is a schematic flowchart showing an example of the short-circuit determination process according to the third embodiment.

A short-circuit determination process according to the third embodiment will be described with reference to the flowchart shown in FIG. 10.

In step S301, the control circuit 210 resets the counter C to 0. Further, the timer for measuring a determination period is started. In step S302, the control circuit 210 acquires a resistance value that is a value of electrical resistance between the probe 122 and the electrode 136. In step S303, the control circuit 210 computes a variation width that is a difference between the currently-acquired resistance value and the last-acquired resistance value.

In step S304, the control circuit 210 determines whether or not the computed variation width is larger than a predetermined threshold value (variation threshold value). When the variation width is not larger than the variation threshold value, the process proceeds to step S306. When the variation width is larger than the variation threshold value, the process proceeds to step S305. In step S305, the control circuit 210 increases the value of the counter C. After that, the process proceeds to step S306.

In step S306, the control circuit 210 determines whether or not a predetermined determination period has elapsed. When the determination period has not elapsed, the process returns to step S302. In other words, the process from step S302 to step S306 is repeated, and the number of times the variation width is detected as being larger than the variation threshold value is counted as a value of the counter C.

When it is determined in step S306 that the determination period has elapsed, the process proceeds to step S307. In step S307, the control circuit 210 determines whether or not the value of the counter C is larger than the reference number of times N. When the value of the counter C is not larger than the reference number of times N, the process returns to step S301. In other words, the counter C is reset to 0, and the number of cases where the variation width is larger than the variation threshold value is counted again during the determination period. It is thus determined whether the number of times the variation width is larger than the variation threshold value is larger than the reference number of times N for each determination period.

When the value of the counter C is larger than the reference number of times N in step S307, the process proceeds to step S308. When the probe 122 and the electrode 136 are determined as being short-circuited, the process proceeds to step S308. In step S308, the control circuit 210 performs error processing. Thus, the short-circuit determination process is completed.

Also, according to the third embodiment, a short circuit between the probe 122 and the electrode 136 can be detected appropriately even while the probe 122 is ultrasonically vibrating, as in the first embodiment.

Fourth Embodiment

A fourth embodiment will be described. In the fourth embodiment, the elements that are different from those of the first embodiment will be described, and the elements that are the same as those of the first embodiment are denoted by the same signs and their descriptions will be omitted. In the first embodiment, it is determined whether or not a short circuit occurs based on the number of times the resistance value becomes less than the resistance threshold value during the determination period. In contrast, in the fourth embodiment, a variation of the resistance value caused by ultrasonic vibration is eliminated through a low pass filter to determine whether a short circuit occurs based on a signal processed through the filter.

Figure 11:
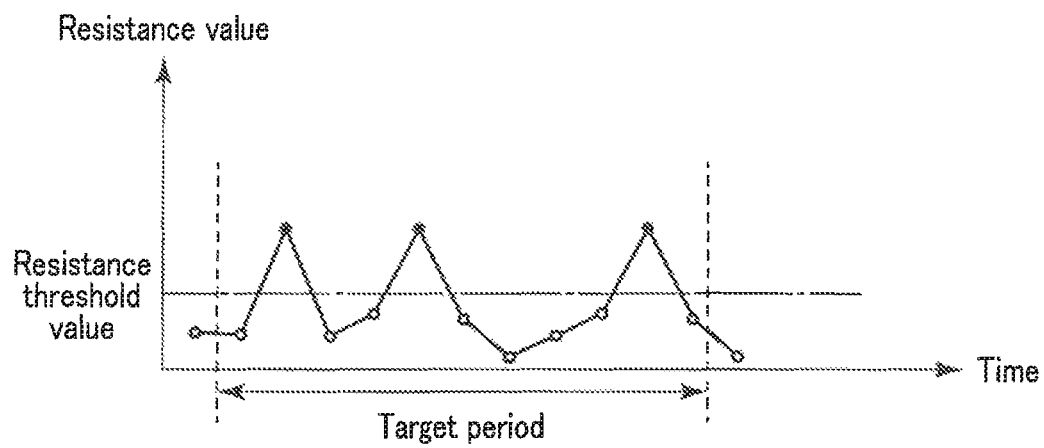
FIG. 11 is a schematic diagram for explaining a short-circuit determination process according to a fourth embodiment.
Figure 12:
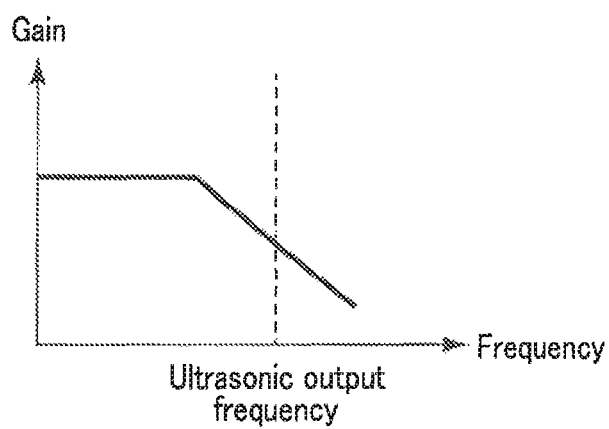
FIG. 12 is a schematic diagram for explaining the short-circuit determination process according to the fourth embodiment.
Figure 13:
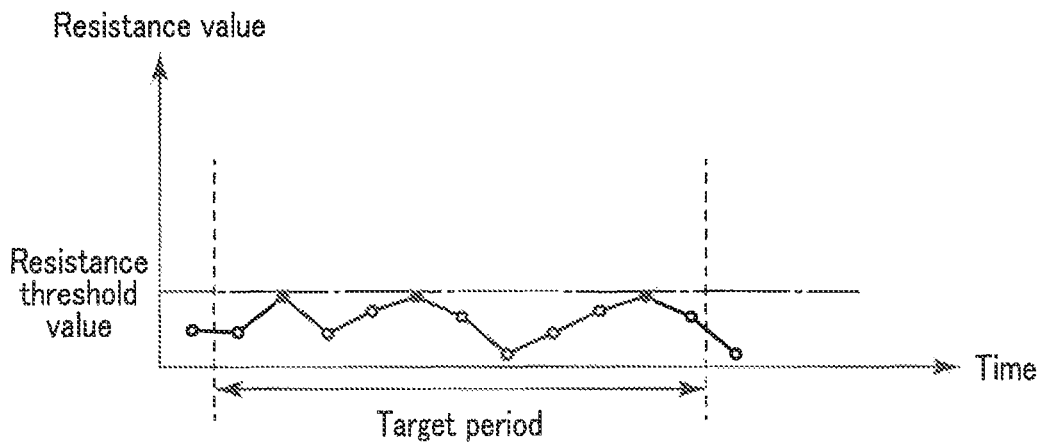
FIG. 13 is a schematic diagram for explaining the short-circuit determination process according to the fourth embodiment.

FIG. 11 shows a variation of resistance values over time. As shown in FIG. 11, for example, a signal including a high-frequency component derived from ultrasonic vibration is processed through a low pass filter. The low pass filter used here is a low pass filter having gain characteristics, for example, as shown in FIG. 12, to cut off the output frequency for vibrating the probe 122 ultrasonically, or the vibration frequency of the probe 122. The signal processed through the low pass filter is shown in FIG. 13, for example. In the fourth embodiment, it is determined that a short circuit occurs for the signal processed through the low pass filter when the fact that the resistance value becomes less than the threshold value continues for a predetermined period.

FIG. 14 is a schematic block diagram showing an example of the configuration of the operating system 10 according to the fourth embodiment. As shown in this figure, the operating system 10 of the fourth embodiment differs from that of the first embodiment in the configuration of the control circuit 210. The other configurations of the operating system 10 of the fourth embodiment are the same as those of the operating system 10 of the first embodiment.

Like the control circuit 210 of the first embodiment, the control circuit 210 of the fourth embodiment includes an output control circuit 212 and a resistance acquisition circuit 214. The control circuit 210 of the fourth embodiment also includes a filter 222 and a determination circuit 224.

As in the first embodiment, the output control circuit 212 controls the output of the ultrasonic drive circuit 232 and that of the high-frequency drive circuit 234. The output control circuit 212 transmits information on the control of outputs of the ultrasonic drive circuit 232 and high-frequency drive circuit 234 to the determination circuit 224.

As in the first embodiment, the resistance acquisition circuit 214 acquires a resistance value of electrical resistance between the probe 122 and the electrode 136 based on a voltage value and a current value acquired from the voltage detection circuit 242 and the current detection circuit 244 through the A/D converter 246. A signal indicating the resistance value is transmitted to the filter 222.

The filter 222 is a low pass filter to cut off the frequency of a signal to vibrate the ultrasonic vibrator 188, which is output from the ultrasonic drive circuit 232. The filter 222 may be an analog filter circuit to filter an analog signal indicating a resistance value, or a digital filter to filter a signal digitized by acquiring an analog signal indicating a resistance value as a discrete value. The cut-off frequency of the filter 222 is determined based on the vibration frequency of the probe 122. The signal that has passed through the filter is transmitted to the determination circuit 224.

The determination circuit 224 determines whether or not a state in which the resistance value is not larger than the predetermined resistance threshold value continues for a predetermined period with respect to the signal received from the filter 222, and thus determines whether or not the probe 122 and the electrode 136 are short-circuited.

Figure 15:
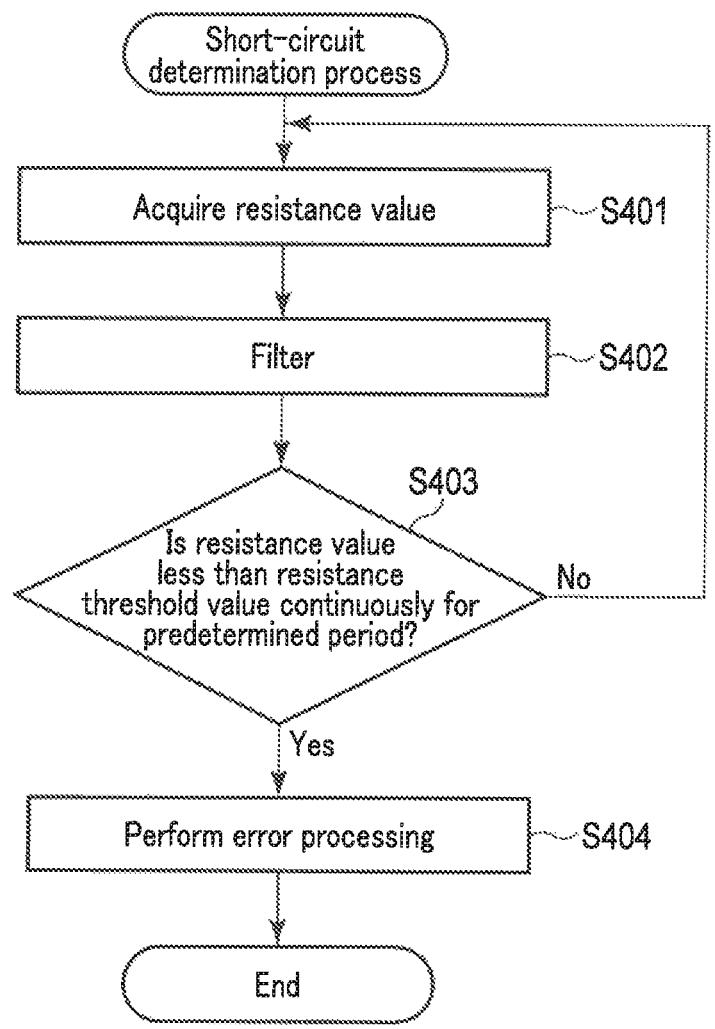
FIG. 15 is a schematic flowchart showing an example of the short-circuit determination process according to the fourth embodiment

A short-circuit determination process according to the fourth embodiment will be described with reference to the flowchart shown in FIG. 15.

In step S401, the control circuit 210 acquires a resistance value that is a value of electrical resistance between the probe 122 and the electrode 136. In step S402, the control circuit 210 filters a signal with the resistance value acquired in step S401, through a low pass filter.

In step S403, the control circuit 210 determines whether or not the fact that the filtered resistance value is less than the resistance threshold value is observed continuously for a predetermined period. If the condition is not satisfied, the process returns to step S401. If the condition is satisfied, the process proceeds to step S404.

In step S404, the control circuit 210 performs error processing. Thus, the short-circuit determination process is completed.

According to the fourth embodiment, a high-frequency signal derived from the ultrasonic vibration of the probe 122, and thus a short circuit between the probe 122 and the electrode 136, can be detected appropriately.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A power supply apparatus for a treatment instrument that includes a probe having electrical conductivity which vibrates, a grasping member that is opened and closed with respect to the probe and an electrode provided in the grasping member, the apparatus supplying high-frequency power between the probe and the electrode, the apparatus comprising:
    an ultrasonic drive circuit configured to supply power to the probe to generate ultrasonic vibrations;
    a resistance acquisition circuit which repeatedly acquires a resistance value of electrical resistance between the probe and the electrode;
    a counter indicating a number of times the resistance value satisfies a predetermined condition;
    a condition determination circuit which increments the counter each time the resistance value satisfies the predetermined condition while the probe is vibrating and power is supplied between the probe and the electrode; and
    a determination circuit which:
        repeatedly acquires a time that has elapsed after acquiring the resistance value,
        determines whether a determination period has elapsed based on the acquired time, and
        determines that the probe and the electrode are electrically short-circuited based on: (i) a total of the counter exceeding a predetermined reference number, and (ii) the determination period being elapsed.

2. The power supply apparatus according to claim 1, wherein
    the resistance acquisition circuit acquires the resistance value at predetermined sampling time intervals based on the high-frequency power supplied between the probe and the electrode,
    the condition determination circuit compares the resistance value with a predetermined threshold value to acquire the number of times the predetermined condition is satisfied, and
    the determination circuit determines that the probe and the electrode are electrically short-circuited when the number of times exceeds the predetermined reference number of times during a predetermined determination period.

3. The power supply apparatus according to claim 1, wherein
    the condition determination circuit compares the resistance value with a predetermined threshold value to acquire the number of times that the resistance value becomes less than the predetermined threshold value, and
    the determination circuit determines that the probe and the electrode are electrically short-circuited when the number of times exceeds the predetermined reference number of times during a predetermined determination period.

4. The power supply apparatus according to claim 1, wherein the resistance acquisition circuit acquires the resistance value at sampling time intervals shorter than a vibration period of the probe.

5. The power supply apparatus according to claim 4, wherein
    the condition determination circuit acquires the number of times a resistance value obtained during a target period based on the vibration period becomes less than a predetermined threshold value with reference to a time when the resistance value becomes less than the predetermined threshold value, and
    the determination circuit determines that the probe and the electrode are electrically short-circuited when the number of times exceeds the predetermined reference number of times during a predetermined determination period.

6. The power supply apparatus according to claim 5, wherein the target period is a predetermined period set for each vibration period with reference to a time when the resistance value becomes less than the predetermined threshold value.

7. The power supply apparatus according to claim 1, wherein
    the resistance acquisition circuit acquires the resistance value at predetermined sampling time intervals,
    the condition determination circuit acquires the number of times a variation width of the resistance value exceeds a predetermined threshold value, and
    the determination circuit determines that the probe and the electrode are electrically short-circuited when the number of times exceeds the predetermined reference number of times during a predetermined determination period.

8. An operating system comprising:
    the power supply apparatus according to claim 1; and
    the treatment instrument.

9. The power supply apparatus according to claim 2, wherein the predetermined determination period is longer than a vibration period of the probe.

10. The power supply apparatus according to claim 9, wherein at least one sampling time interval during which the resistance value is acquired is shorter than the vibration period of the probe.

11. The power supply apparatus according to claim 1, further comprising;
    a timer that measures the time that has elapsed after acquiring the resistance value.

12. A power supply apparatus for a treatment instrument that includes a probe having electrical conductivity which vibrates, a grasping member that is opened and closed with respect to the probe and an electrode provided in the grasping member, the apparatus supplying high-frequency power between the probe and the electrode, the apparatus comprising:
    an ultrasonic drive circuit configured to supply power to the probe to generate ultrasonic vibrations a resistance acquisition circuit which repeatedly acquires a resistance value of electrical resistance between the probe and the electrode;

a counter indicating a number of times the resistance value satisfies a predetermined condition;

a condition determination circuit that increments the counter each time a signal of the resistance value satisfies the predetermined condition for a predetermined period while the probe is vibrating and power is supplied between the probe and the electrode, the signal of the resistance value being filtered by a filter and whose cut-off frequency is determined based on a vibration frequency of the probe; and a determination circuit which:
   repeatedly acquires a time that has elapsed after acquiring the resistance value,
   determines whether a determination period has elapsed based on the acquired time, and
   determines that the probe and the electrode are electrically short-circuited based on: (i) a total of the counter exceeding a predetermined reference number, and (ii) the determination period being elapsed.

13. A method of operating a power supply apparatus for a treatment instrument including a probe having electrical conductivity which vibrates, a grasping member that is opened and closed with respect to the probe and an electrode provided in the grasping member, the apparatus supplying high-frequency power between the probe and the electrode, the method causing the power supply apparatus to:

supply power, by an ultrasonic drive circuit, to the probe to generate ultrasonic vibrations;

repeatedly acquire a resistance value of electrical resistance between the probe and the electrode;

increment a counter each time the resistance value satisfies a predetermined condition while the probe is vibrating and power is supplied between the probe and the electrode, the counter indicating the number of times the resistance value satisfies the predetermined condition;

repeatedly acquire a time that has elapsed after acquiring the resistance value;

determine whether a determination period has elapsed based on the acquired time; and determine that the probe and the electrode are electrically short-circuited based on: (i) a total of the counter exceeding a predetermined reference number, and (ii) the determination period being elapsed.

* * * * *